(12) United States Patent
Nakata et al.

(10) Patent No.: US 7,732,212 B1
(45) Date of Patent: Jun. 8, 2010

(54) METHOD OF MANAGEMENT OF ANALYTICAL DATA AND SYSTEM FOR MANAGEMENT OF ANALYTICAL DATA

(75) Inventors: Shinpei Nakata, Mito (JP); Takehiko Yotsugi, Hitachinaka (JP); Hiroaki Ishizawa, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 711 days.

(21) Appl. No.: 09/936,918

(22) PCT Filed: Mar. 3, 2000

(86) PCT No.: PCT/JP00/01280

§ 371 (c)(1),
(2), (4) Date: Nov. 1, 2001

(87) PCT Pub. No.: WO01/67113

PCT Pub. Date: Sep. 13, 2001

(51) Int. Cl.
*G01N 33/48* (2006.01)

(52) U.S. Cl. .............................. 436/43; 436/45; 422/62; 422/63; 422/67; 422/68.1

(58) Field of Classification Search .................... 422/62, 422/63, 67, 68.1, 99; 436/43, 45
See application file for complete search history.

(56) References Cited

U.S. PATENT DOCUMENTS 5,690,893 A 11/1997 Ozawa et al.
6,022,746 A * 2/2000 Fritchie et al. ................ 436/50
2002/0150450 A1 * 10/2002 Bevirt et al. ........... 414/225.01

FOREIGN PATENT DOCUMENTS

| DE | 43 12 093 A1 | 10/1993 |
| EP | 0 510 686 A2 * | 10/1992 |
| JP | 04-128657 | 4/1992 |
| JP | 5-288756 | 11/1993 |
| JP | 11-211731 | 8/1999 |
| WO | WO 99/22236 | 5/1999 |

* cited by examiner

*Primary Examiner*—Lyle A Alexander
(74) *Attorney, Agent, or Firm*—Mattingly & Malur, P.C.

(57) ABSTRACT

A communication unit (12) of a service center (10) transmits and receives information such as analysis information to and from a plurality of automatically analyzing apparatuses (100). A database (16) stores the information such as the analysis information. An analysis information parsing unit (14) evaluates and parses results of analyses made by the automatically analyzing apparatuses using the analysis information stored in the database. The reagent parameter registration unit (18) registers information on reagents in the database (16). The communication unit (12), responsive to a request from an automatically analyzing apparatus, retrieves information on analysis parameters related to managed reagents from the database for transfer to the automatically analyzing apparatus. In this way, analysis parameters can be readily set for a testing item to be analyzed using a reagent.

9 Claims, 5 Drawing Sheets

FIG.4

REAGENT SCREEN — 172A

| POSITION | TESTING ITEM NAME | REAGENT TYPE | REAGENT LOT NO. | REAGENT BOTTLE NO. | PRESENCE/ ABSENCE OF ANALYSIS PARAMETERS | REAGENT INFORMATION SERIAL NO. |
|---|---|---|---|---|---|---|
| 1 | ALP | R1 | 100001 | 10001 | ○ | |
| 2 | ALP | R2 | 100001 | 10002 | ○ | |
| 3 | | R1 | 100010 | 10010 | | |
| 4 | | | | | | |
| .. | | | | | | |

[ REAGENT LIST DOWN LOAD ]   [ PARAMETER DOWNLOAD ]

FIG.5

REAGENT LIST SCREEN — 172B

| REAGENT INFORMATION SERIAL NO. | REAGENT MAKER NAME | TESTING ITEM NAME | REAGENT LOT NO. | ... | | |
|---|---|---|---|---|---|---|
| 2001 | AAA | AST | 00001 | | | |
| 2002 | AAA | AST | 00002 | | | |
| 2003 | BBB | AST | 00010 | | | |
| .. | | | | | | | ately analyzing apparatus in all testing facilities to which their reagents are supplied. Therefore, the number of work steps is increased with an increase in a plurality of automatically analyzing apparatuses or a plurality of testing facilities, and correspondingly automatically analyzing apparatuses.

METHOD OF MANAGEMENT OF ANALYTICAL DATA AND SYSTEM FOR MANAGEMENT OF ANALYTICAL DATA

FIELD OF THE INVENTION

The present invention relates to an analysis information management method and an analysis information management system, and more particularly, to an analysis information management method and an analysis information management system which are suitable for automatically setting analysis parameters required for conducting an analysis into an analyzer.

BACKGROUND ART

An automatically analyzing apparatus relies on a chemical reaction of a sample and a reagent introduced into an reaction container to quantitatively measure contents of the sample. For using the automatically analyzing apparatus, analysis parameters must be set into the automatically analyzing apparatus as analysis conditions, requiring a large number of steps for this work. Here, the analysis parameters refer to parameters for each testing item in the automatically analyzing apparatus, and basically include information such as the amount of dispensed sample, reagents used for an analysis and amounts thereof, the wavelength of absorbance under measurement, the type of reaction process and a method of calculating a concentration, a standard sample and known concentration for use in a calibration, and the like. The information relates to reagents, and differs from one another depending on reagent makers dedicated to the manufacturing even for reagents used for analyzing the same testing item. In addition, even with reagents manufactured by the same reagent maker, contents of analysis parameters may result in different information for different manufacturing lots. Thus, analysis parameters to be set must be always the latest analysis parameters related to reagents set in the automatically analyzing apparatus.

As a first method of setting analysis parameters into an automatically analyzing apparatus, for example, as described in JP-A-11 211731, it is known that user sets parameters through a keyboard or the like as initial settings. Also, as a second method, for example, as described in JP-A-5-288756, it is known that reagent identification bar codes adhered on reagent containers are read by a bar code reader, and a variety of parameters are read from a computer based on identification codes inscribed in the bar codes to set the parameters into an automatically analyzing apparatus.

DISCLOSURE OF THE INVENTION

Here, the parameter setting method described in JP-A-11-211731 implies problems that a large number of input steps are required since parameters are manually set from a keyboard, and that correct parameter settings may not be made in some cases due to erroneous inputs and the like. Particularly, in recent automatically analyzing apparatuses, the number of parameters and the number of screens for setting the parameters tend to increase due to the advancement of their functions, so that special knowledge is required for setting them without errors. Actually, dedicated persons in a reagent supplier or the like may occasionally set parameters, conduct subsequent calibration and measurements of accuracy management samples for confirming the operation before the parameters are provided to users. In this event, the reagent suppliers must set parameters for all automatically analyzing apparatus in all testing facilities to which their reagents are supplied. Therefore, the number of work steps is increased with an increase in a plurality of automatically analyzing apparatuses or a plurality of testing facilities, and correspondingly automatically analyzing apparatuses.

On the other hand, the parameter setting method described in JP-A-5-288756 reads parameter information from an external computer based on bar codes adhered on reagent containers for automatic settings, wherein, however, a problem arises that bar codes must be adhered on reagent containers. In addition, after setting analysis parameters, the user is required to have special knowledge for determining whether or not the settings have been correctly made.

It is an object of the present invention to provide an analysis information management method and an analysis information management system which are capable of readily setting analysis parameters for testing items subjected to an analysis using a reagent.

To achieve the above object, in a service center having a database connected to a plurality of automatically analyzing apparatus used in a plurality of facilities through communication lines for storing analysis parameters related to a plurality of reagents for use in the plurality of automatically analyzing apparatus used in the plurality of facilities, the present invention transfers analysis parameters for a testing item to be analyzed using a reagent to an automatically analyzing apparatus through the communication line in response to a request from the automatically analyzing apparatus. This method can readily set required analysis parameters even if a reagent container does not have means such as a bar code which allows identification of a reagent contained therein.

Also, to achieve the above object, the present invention comprises a communication unit for transmitting and receiving to and from a plurality of automatically analyzing apparatuses information such as information on analyses performed by the respective automatically analyzing apparatuses, a database for storing information such as the analysis information, an analysis information parsing unit for evaluating and parsing results analyzed by the automatically analyzing apparatuses using the analysis information stored in the database, and a reagent parameter registration unit for registering information on reagents in the database, wherein the communication unit retrieves information on analysis parameters related to a managed reagent from the database in response to a request from the automatically analyzing apparatus, and transfers the information to the automatically analyzing apparatus. This configuration can readily set required analysis parameters even if a reagent container does not have means such as a bar code which allows identification of a reagent contained therein.

BRIEF DESCRIPTION OF THE DRAWINGS

FIG. 4 is an explanatory diagram of a reagent information screen in the analysis parameter setting process according to one embodiment of the present invention; and FIG. 5 is an explanatory diagram of a reagent listing screen in the analysis parameter setting process according to one embodiment of the present invention.

BEST MODE FOR CARRYING OUT THE INVENTION

In the following, an analysis information management method and an analysis information management system according to one embodiment of the present invention will be described with reference to FIGS. 1 to 5.

First, the configuration of a system for use with the analysis information management method according to this embodiment will be described with reference to FIG. 1.

Figure 1:
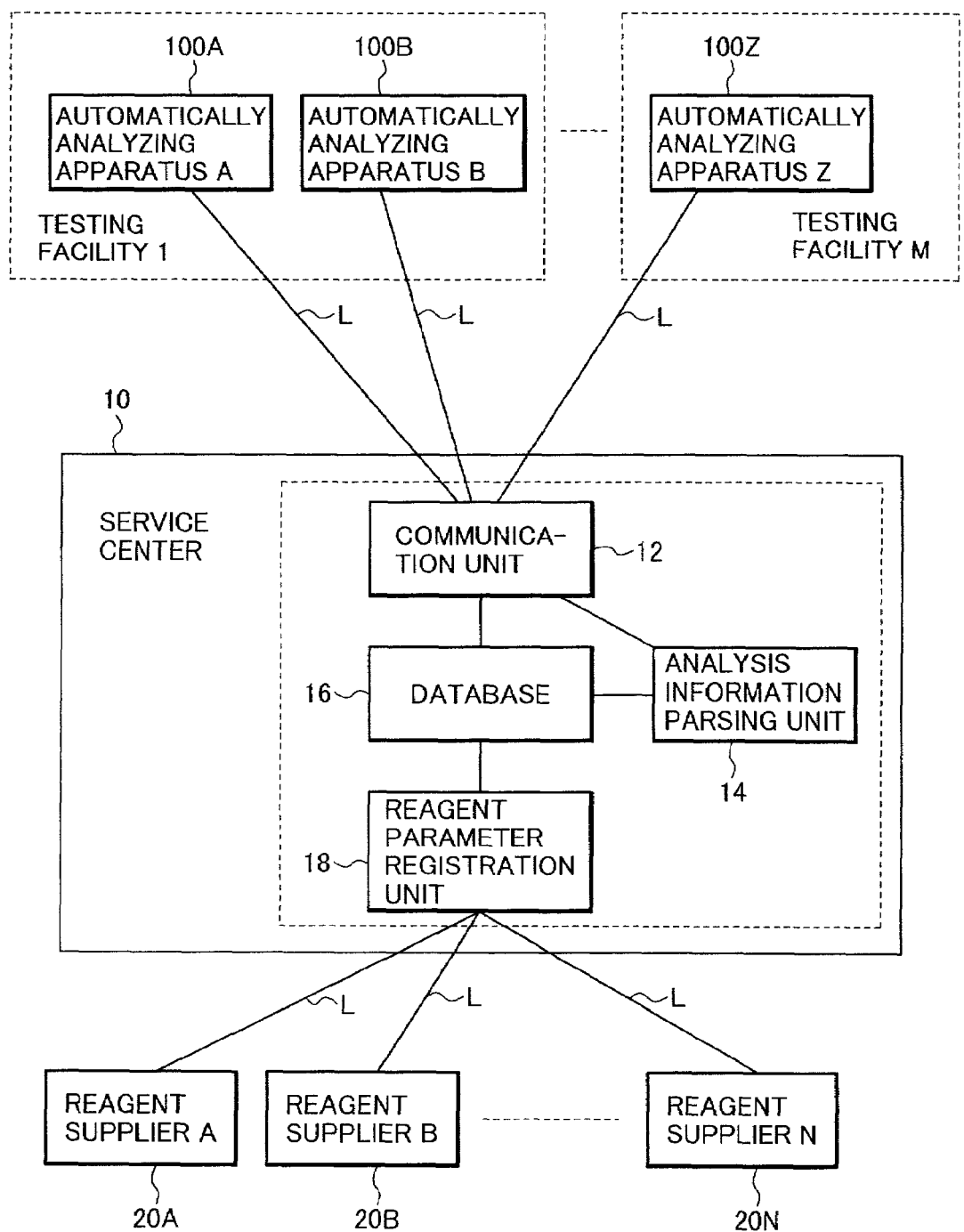
FIG. 1 is a block diagram illustrating the configuration of an analysis information management system using an analysis information management method according to one embodiment of the present invention.

FIG. 1 is a block diagram illustrating the configuration of an analysis information management system which uses the analysis information management method according to one embodiment of the present invention.

A service center 10 is connected to all automatically analyzing apparatuses 100A, 100B, . . . , 100Z in testing facilities, which have concluded a service agreement, through communication lines L. In each of the testing facilities, one or a plurality of automatically analyzing apparatuses 100 are installed such that the automatically analyzing apparatuses 100A, 100B are installed in a testing facility 1, and the automatically analyzing apparatus 100Z is installed in a testing facility M. The service center 10 is also connected to a plurality of reagent suppliers 20A, 20B, . . . , 20N through the communication lines L.

The service center 10 intensively manages analysis information such as analysis parameters related to reagents, results of analyses made by the respective automatically analyzing apparatuses, and the like. The service center 10 comprises a communication unit 12, an analysis information parsing unit 14, a database 16, and a reagent parameter registration unit 18.

The communication unit 12 transmits and receives analysis information between the automatically analyzing apparatuses 100 connected thereto through the communication lines L. The analysis information parsing unit 14 evaluates and parses analysis information such as results of analyses sent thereto from the connected automatically analyzing apparatuses 100. The database 16 is connected to the automatically analyzing apparatuses 100 through the communication lines L for unitarily managing all reagents available in all the associated automatically analyzing apparatuses 100 and analysis parameters related to the reagents, and analysis information on the associated automatically analyzing apparatuses 100, for example, information such as reagents used in analyses and analysis parameters, results of calibrations, results of analyses on accuracy management samples, and the like. The reagent parameter registration unit 18 is a unit for registering information related to reagents such as reagent information comprised of the names of testing items under analysis using reagents, reagent lot Nos, and the like, analysis parameters related to the reagents, and automatically analyzing apparatuses available with the reagents, and the like in the database 16.

The reagent suppliers 20 are dealers which supply their reagents to the respective facilities. The reagent suppliers 20 have concluded an agreement with the service center 10, in which the reagent suppliers 20 register the database 16 of the service center 10 through the reagent parameter registration unit 18 when their reagents or analysis parameters related to the reagents need be added or updated, within those available to all the automatically analyzing apparatuses 100 administered by the service center 10, due to the development of new reagents capable of analyzing new testing items, and a change in manufacturing lots of reagents even if they are used for existing testing items. In this way, the service center 10 holds the most recent information related to reagents.

In the automatically analyzing apparatus 100, analysis parameters must have been set for testing items which are to be analyzed using reagents set in the automatically analyzing apparatus 100 before starting the analysis. For setting a novel reagent supplied newly from a reagent supplier 20 into the automatically analyzing apparatus 100, associated analysis parameters may not have been set in the automatically analyzing apparatus 100. In this event, the automatically analyzing apparatus 100 performs an operation for requesting the service center 10 to send through the communication line L a list on which one can view all reagents available for the automatically analyzing apparatus 100. The service center 10 searches the database 16 to create a list of reagents available in the automatically analyzing apparatus 100, which has made the request, from among the database 16, and transmits the list to the automatically analyzing apparatus 100 through the communication line L. The automatically analyzing apparatus 100 displays the received reagent list. As the user selects a reagent set in the automatically analyzing apparatus 100 from the list, the automatically analyzing apparatus 100 transmits the selected information to the service center 10. Upon receipt of the selected information, the service center 10 searches the database 16 for associated analysis parameters which are sent to the automatically analyzing apparatus 100 through the communication line L. The automatically analyzing apparatus 100 sets the received analyzing parameters.

While in the foregoing example, the reagent list is transmitted to the automatically analyzing apparatus 100, the service center 10 may have a home page for registering the reagent list such that the list can be viewed from the automatically analyzing apparatus 100.

Next, the configuration of an automatically analyzing apparatus for use in the analysis information management system according to this embodiment will be described with reference to FIG. 2.

Figure 2:
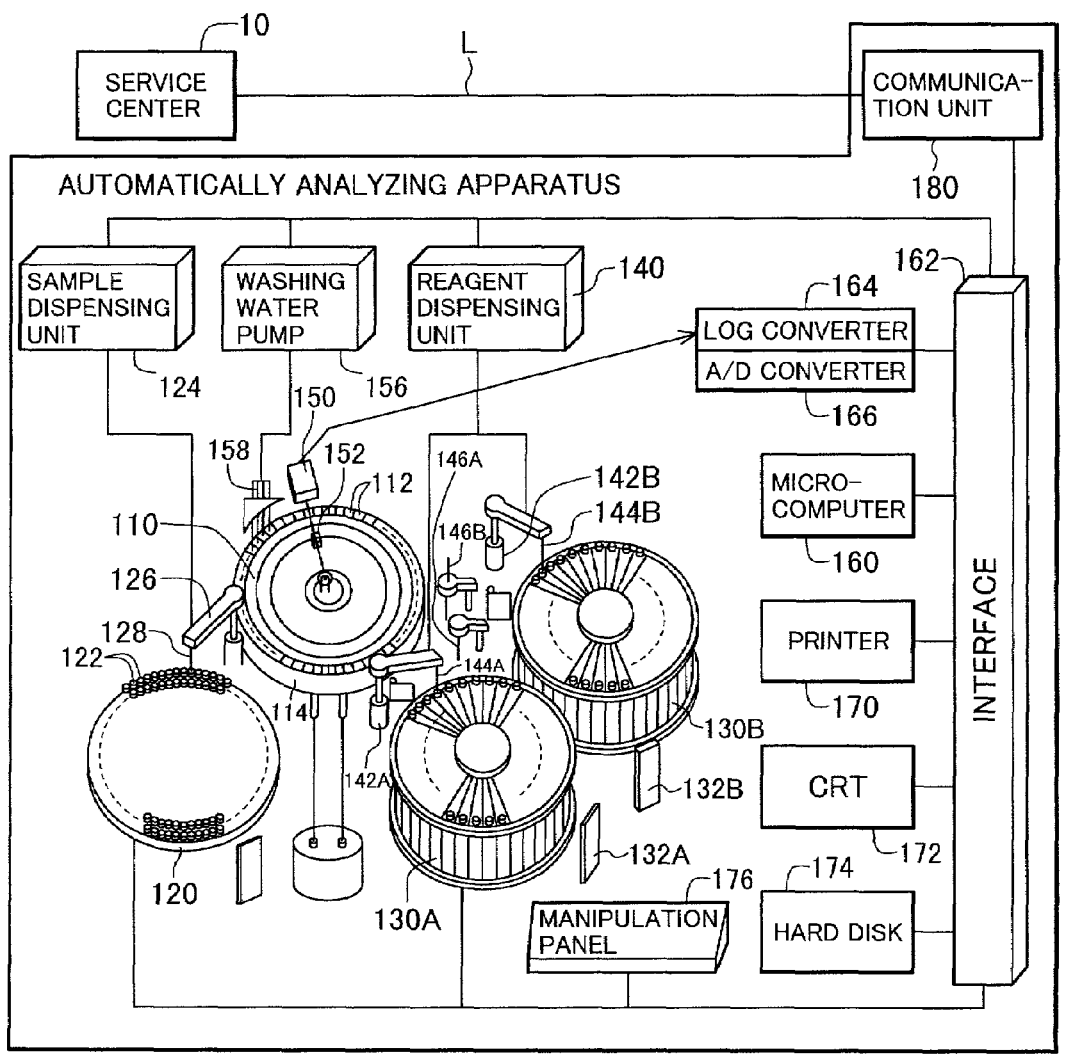
FIG. 2 is an apparatus configuration diagram illustrating the configuration of an automatically analyzing apparatus for use in the analysis information management system according to one embodiment of the present invention.

FIG. 2 is an apparatus configuration diagram illustrating the configuration of the automatically analyzing apparatus for use in the analysis information management system according to one embodiment of the present invention.

A reaction container 112 is provided on the outer periphery of a reaction disk 110. The entire reaction disk 110 is held at a predetermined temperature by an incubation bath 114. A large number of sample cups 122 are disposed in a sample disk unit 120. A sample in a sample cup 122 is extracted as required through a nozzle 128 of a sample pipetting unit 126 which is controlled by a sample dispensing unit 124, and injected into the reaction container 112 at a sample dispensing position.

Reagent bottles with bar code labels are disposed in reagent disk units 130A, 130B. A bar code reader 132A, 132B is associated with each of the reagent disk units 130A, 130B for reading a bar code upon registration of a reagent to register reagent bottle information corresponding to a position. The reagent bottle information is comprised of information such as the type of reagent, lot No., expiration date, remaining reagent amount, and the like.

Each of the reagent disks is also provided with a second reagent pipetting unit 142A and a first reagent pipetting unit 142B controlled by the sample dispensing unit 140. The second reagent pipetting unit 142A pipets a reagent from the reagent disk using a nozzle 144A, and delivers it to the reaction container 112. The first reagent pipetting unit 142B in turn pipets a reagent from the reagent disk using a nozzle 144B and delivers it to the reaction container 112. Stirrers 146A, 146B are disposed in close proximity to the reagent disk units 130A, 130B for stirring a sample and a reagent within the reaction container 112. The reaction container 112 which contains an object under photometry is disposed between an analysis unit comprised of a multi-wavelength photometer 150 and a light source 152. A washing unit 158 washes the reaction container 112 with a washing solution supplied from a washing water pump 156.

Further, as a control system and a signal processing system, the automatically analyzing apparatus 100 comprises a microcomputer 160, an interface 162, a Log (logarithm) converter 164, and an A/D converter 166. Also, the automatically analyzing apparatus 100 comprises a printer 170 for printing, a CRT 172 for display, a hard disk 174 as a storage device, and a manipulation panel for inputting (a keyboard or a pointing device such as a touch screen, a mouse, and the like) 176. The automatically analyzing apparatus 100 further comprises a communication unit 180 for communicating with the service center 10 through the communication line L.

Next, description will be made on the operation of the automatically analyzing apparatus 100 illustrated in FIG. 2.

A sample put in a sample cup 122 is dispensed to the reaction container 112 by a predetermined amount using the nozzle 128 of the sample pipetting unit 126 in accordance with analysis parameters stored in a memory of the microcomputer 160.

Next, the reaction container 112 dispensed with the sample is transported to a reagent dispensing position by rotating the reaction disk 110. Subsequently, reagents are inputted through the manipulation panel 176, and are dispensed by predetermined amounts to the reaction container 112, dispensed with the sample, using the nozzles 144A, 144B of the reagent pipetting units 142A and 142B in accordance with analysis parameters stored in the microcomputer 160. Subsequently, the sample and reagents are stirred by the stirrers 146A, 146B for mixing.

When the reaction container 112 traverses a photometric position, the multi-wavelength photometer 150 measures the absorption. The measured absorption is captured into the microcomputer 160 through the Log converter 164, A/D converter 166 and interface 162. The absorption is converted to concentration data based on a calibration curve created from the absorption of a standard sample solution which has been previously measured by an analysis method specified for each item. The measured component concentration data is outputted to the printer 170 and to a screen of the CRT 172. The result of measurement may also be transmitted to the outside through the communication unit 180.

In the foregoing measurement principles, the user performs on the screen (CRT) 172 settings of various parameters required for the measurement, registration of the sample, and confirmation of the result of analysis.

Reagent bottles may or may not have a bar code adhered on the side surface thereof. A reagent bar code describes reagent bottle identification information, reagent lot No., expiration date, and the like. As illustrated in FIG. 2, when the reagent bar code readers 132A, 132B are provided, bar codes are read from reagent bottles at all positions on the reagent disks, for example, when the reagent disks 130A, 130B are closed with lids, to register reagent bottle information corresponding to each of the positions. On the other hand, when bar codes are not adhered on bottles, reagent bottle information is registered by the user who manually enters information included in bar codes from the manipulation panel 176. The reagent bottle information is comprised of information such as the type of reagent, lot No., expiration date, remaining amount of reagent, and the like. Testing items available for analysis are determined by reagents set in the reagent disks 130A, 130B, and analysis parameters are required for defining analysis conditions therefor. Also, other methods of setting analysis parameters may involve specifying testing items and manually entering required parameters from the manipulation panel 176, reading parameters from FD or bar sheet, and the like.

Next, the contents of analysis parameter setting process in the analysis information management method according to this embodiment will be described with reference to FIGS. 3 to 5.

First, the contents of the analysis parameter setting process according to this embodiment will be described with reference to FIG. 3.

Figure 3:
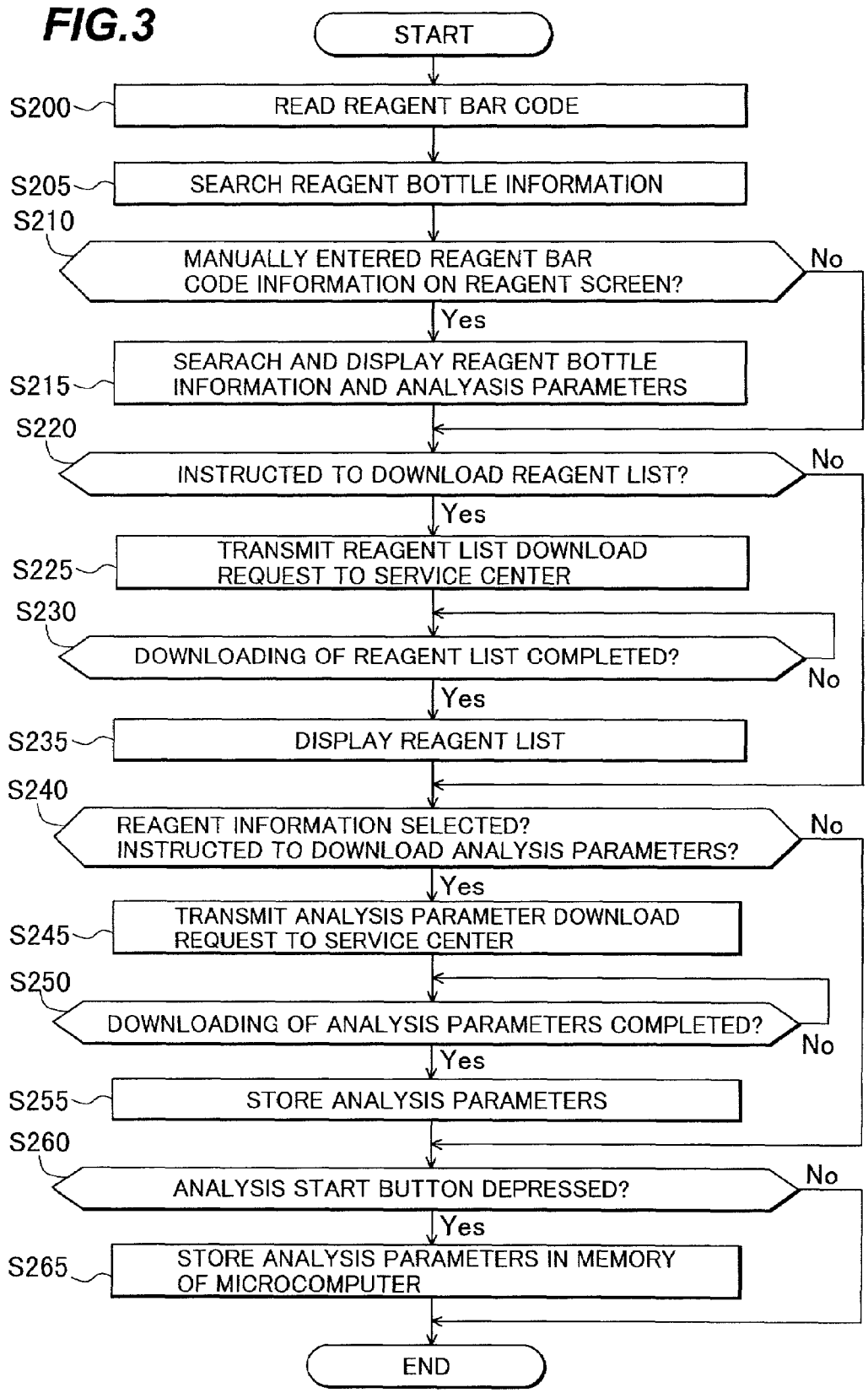
FIG. 3 is a flow chart illustrating the contents of an analysis parameter setting process according to one embodiment of the present invention.

FIG. 3 is a flow chart illustrating the contents of the analysis parameter setting process according to one embodiment of the present invention.

Here, description will be made on the contents of the process from setting of reagent bottles on the reagent disks 130A, 130B of the automatically analyzing apparatus 100 to setting of analysis parameters associated therewith.

At step s200, the operator sets reagent bottles on the reagent disks 130A, 130B of the automatically analyzing apparatus 100, and for example, closes the lids of the reagent disks 130A, 130B, causing the microcomputer 160 of the automatic analysis apparatus 100 to read bar codes on the reagent bottles at all positions on the reagent disks 130A, 130B from the bar code readers 132A, 132B.

Then, at step s205, the microcomputer 160 searches stored reagent bottle information and analysis parameter information from the read bar code information.

Assuming herein that a reagent screen is opened at the automatically analyzing apparatus 100, the CRT 172 displays on a reagent information screen 172A information related to the reagent set at each of the positions on the reagent disks, for example, as illustrated in FIG. 4.

Here, referring to FIG. 4, an example of reagent information screen will be described in this embodiment.

FIG. 4 is an explanatory diagram of the reagent information screen in the analysis parameter setting process according to one embodiment of the present invention.

The reagent information screen 172A is comprised of Position, Testing Item, Reagent Type, Reagent Lot No., Reagent Bottle No., Presence/Absence of Analysis Parameters, Reagent Information Serial #, and the like. Position indicates the position at which a reagent bottle is set on the reagent disk units 130A, 130B, and gives a serial number such as No. 1, No. 2, and the like, by way of example. The shown example indicates a reagent set at Position 1 has a testing item name "ALP," reagent type "R1," reagent lot No. "100001," reagent bottle No. "10001," and analysis parameters "presence." The reagent information serial # will be described later with reference to FIG. 5. For example, for a reagent at Position "3," the table shows that analysis parameters are "absent." Also, at Position "4," the table does not at all display information such as Position, Testing Item, Reagent Type, Reagent Lot No., Reagent Bottle No., Presence/Absence of Analysis Parameters, and the like, meaning that no bar code is adhered on a reagent bottle, so that the information is displayed as blank.

When no bar code is adhered on a reagent bottle, for example, as Position 4, the operator sees the reagent bottle and enters information which allows identification of the reagent such as the reagent lot No. or the like in blanked fields on the reagent information screen 172A.

At step s210, the microcomputer 160 determines whether or not reagent bar code information has been manually entered on the reagent screen. The process continues to step s215 when entered, and to step s220 when not entered.

As described above, when information is manually entered for the reagent at Position "4," the microcomputer 160 searches stored reagent bottle information for information on the reagent, and displays the information, if found, on the reagent information screen 172A at step s215. On the other hand, if analysis parameters have been stored for a testing item which is analyzed with the reagent, "presence" is displayed in the field of Presence/Absence of Analysis Parameters. When a novel reagent is set and therefore no associated analysis parameters have been stored, the absence of analysis parameters is displayed as Position 3, in which case analysis parameters must be newly set before an analysis is started. In this event, the operator depresses a "reagent list download button" positioned in a lower right region in the reagent information screen 172A illustrated in FIG. 4.

At step s220, the microcomputer 160 determines whether or not the operator has instructed to download a reagent list. The process continues to step s225 when instructed, and to s240 when not instructed. As described above, as the operator depresses the "reagent list download button," the process continues to step s225 assuming that the operator has instructed to download the reagent list.

At step s225, the microcomputer 160 transmits a reagent list download request to the service center 10 through the communication line L. In this event, the microcomputer 160 also transmits identification information of the automatically analyzing apparatus 100 such as the model number to the service center 10.

The service center 10 searches for all reagents available in the automatically analyzing apparatus 100, which has made the reagent list download request, collects them in the form of list, and transmits the list to the automatically analyzing apparatus 100 through the communication line L.

At step s230, the microcomputer 160 of the automatically analyzing apparatus 100 is monitoring until the reagent list has been downloaded, and upon completion of the downloading, the microcomputer 160 displays a reagent list as in FIG. 5 on the CRT 172 as a reagent list screen 172B at step s235.

Now, an example of the reagent list screen in this embodiment will be described with reference to FIG. 5.

FIG. 5 is an explanatory diagram of the reagent list screen in the analysis parameter setting process according to one embodiment of the present invention.

The reagent list screen 172B is comprised of Reagent Information Serial #, Reagent Maker Name, Testing Item, Reagent Lot No., and the like. Reagent Information Serial # is a serial number for unitarily managing reagents.

The shown example indicates that a reagent having Reagent Information Serial #"20001" has Reagent Maker Name "AAA," Testing Item Name "AST," and Reagent Lot No. "00001." The operator views this reagent list to search for a reagent for which analysis parameters must be newly set, and enters a testing item name and a reagent information serial number in fields at corresponding positions on the reagent screen in FIG. 3. For example, when a reagent at Position "4" in FIG. 4 is manufactured by a reagent maker named "AAA" and used for a testing item labeled "AST," and has Reagent Lot No. "00001," the operator enters "AST" in Testing Item Name, and "2002" in Reagent Information Serial # on Position "4" in FIG. 4. This causes information such as Reagent Type, Reagent Lot No. and the like to be entered automatically. This processing is performed for all reagents for which analysis parameters have not been stored and therefore must be newly set. Upon completion of this processing, the operator depresses a "parameter download button" in a lower right region on the reagent information screen 172A in FIG. 4.

At step s240, the microcomputer 160 of the automatically analyzing apparatus 100 determines whether or not the operator has selected reagent information, and whether or not the operator has instructed to download analysis parameters. The process continues to step s245 when the operator has selected or instructed, and to step s260 when not.

When the operator has selected reagent information or instructed to download analysis parameters, the microcomputer 160 creates an analysis parameter download request which is transmitted to the service center 10 through the communication line L at step s245. The service center 10 searches for all analysis parameters requested for downloading and transmits the analysis parameters to the automatically analyzing apparatus 100.

At step s250, the microcomputer 160 of the automatically analyzing apparatus 100 is monitoring until the requested analysis parameters have been downloaded. Upon completion of the downloading, the microcomputer 160 stores the received analysis parameters at step s255. As the analysis parameters have been stored, "presence" is displayed in the field "Presence/Absence of Analysis Parameters" at the associated position on the reagent information screen 172A shown in FIG. 4.

At step s260, the microcomputer 160 determines whether or not an analysis start key has been depressed. As the analysis start key is depressed, analysis parameters are stored in the memory of the microcomputer 160 upon start of the analysis for conducting the analysis based on the analysis parameters at step s265.

In the foregoing description, when a reagent bar code is adhered on a reagent bottle, the reagent screen is opened after the reagent bar code has been read, resulting in a search made for reagent bottle information and analysis parameters based on the bar code information. If information has been previously stored, the information is displayed as Position 1 or 2 in FIG. 4. On the other hand, if a novel reagent is set on the reagent disk, reagent bottle information is stored. When associated analysis parameters are present, the reagent bottle information is displayed on the screen in a similar manner. If associated analysis parameters have not been stored, "absence" of analysis parameters is displayed as Position 3 in FIG. 4. Even in this event, analysis parameters can be downloaded and set as is the case with a reagent bottle without a bar code adhered thereon.

If a reagent bar code includes information such as the name of the reagent maker, testing item name, and the like which allows identification of analysis parameters, a parameter download request may be automatically made for the reagent, such that analysis parameters can be set without requiring the user to download a reagent list to select associated reagent information.

Next, a method of verifying that analysis parameters have been correctly set in the automatically analyzing apparatus will be described with reference to FIG. 1.

The automatically analyzing apparatus 100 conducts an analysis based on the analysis parameters set at step s265 in FIG. 3. When a new reagent has been introduced and analysis parameters associated therewith have been newly set, the operator actually performs a calibration to create a calibration curve before an accuracy management sample is analyzed. The controller 160 of the automatically analyzing apparatus 100 transmits the result of calibration and the result of analysis on the accuracy management sample, as well as analysis information such as reagents used therein and analysis parameters to the service center 10 through the communication line L.

The service center 10, upon receipt of he analysis information from each automatically analyzing apparatus 100 through the communication unit 12, classifies the received analysis information by testing facilities or automatically analyzing apparatuses, and saves the classified analysis information in the database 16 for management. The analysis information parsing unit 14 of the service center 10 retrieves the results of analyses on accuracy management samples measured using the same reagent, managed in the database 16, and calculates an average value which is defined as a standard value. Then, upon determination that the currently received result of analysis on the accuracy management sample has been acquired using newly set analysis parameters, the analysis information parsing unit 14 calculates a deviation between the previously found standard value and the currently received analysis result, and determines whether or not the deviation is within an allowable range. If the deviation is out of the allowable range, the analysis information parsing unit 14 confirms, for example, whether correct analysis parameters are used for reagents used in the analysis, whether the set parameters are inconsistent in the contents, and the like. Then, the analysis information parsing unit 14 creates a report which summarizes the result of verification, countermeasures to be taken by the user, and the like, and transmits the report to the automatically analyzing apparatus 100.

The operator of the automatically analyzing apparatus, who has received the report, relies on the contents of the report to, for example, start a testing work if no defect is found in the result of verification, and takes action in accordance with the contents of the report if any defect is found.

In the foregoing manner, the analysis information such as information on the results of measurements made by the automatically analyzing apparatus is transmitted to the service center, such that the results are parsed and evaluated in the service center, thereby making it possible to verify the operation of the apparatus from a global view point and to support the user of the automatically analyzing apparatus who does not have special knowledge to readily verify that analysis parameters have been correctly set.

Each time the result of analysis on the accuracy management sample is received, the analysis information parsing unit 14 calculates a standard value and a deviation, and transmits the result of calculation to the automatically analyzing apparatus 100 which has transmitted the result of analysis in the form of report in a similar manner if any defect is found. On the other hand, if no defect is found, the analysis information parsing unit 14 stores the result of calculation in the database 16, and periodically creates a report which is transmitted to the automatically analyzing apparatus 100.

In the foregoing description, the analysis information parsing unit 14 conducts up to the calculation of a deviation between the result of measurement by the automatically analyzing apparatus 100 and the standard value in the entirety, and sends the result of calculation to the automatically analyzing apparatus 100 as a report. Alternatively, the analysis information parsing unit 14 may periodically calculate standard values and the like of all automatically analyzing apparatuses administrated thereby, and periodically send the information to the automatically analyzing apparatuses 100 as technical information. In this way, the operator of the automatically analyzing apparatus 100 can evaluate, for example, the result of measurement of an accuracy management sample based on the technical information, and can verify by himself that newly set analysis parameters are being correctly used.

In the foregoing description, while the database 16 of the service center 10 is configured to manage information on analyses such as reagents, analysis parameters, results of measurements, and the like, the database 16 may store, by version, programs for controlling all automatically analyzing apparatuses administered thereby, in addition to the foregoing information. In this way, for example, as a new reagent is introduced, a specified analysis method is added for each testing item, so that if an addition, update and the like are required for a program for converting to concentration data based on the analysis method, the program can be downloaded from the service center for automatic installation into the automatically analyzing apparatus, as is the case with the analysis parameters. Further, since the database 16 of the service center 10 can also manage information on versions of programs installed in the automatically analyzing apparatuses administered thereby, it is possible to correctly keep track of the current states of the administered automatically analyzing apparatuses and to support a change in programs as mentioned in a timely manner.

As described above, according to this embodiment, even under condition that there are a plurality of facilities having a plurality of automatically analyzing apparatuses using reagents from a plurality of reagent suppliers, even if reagent containers do not have bar codes adhered thereon for allowing identification of reagents therein, it is possible to readily set analysis parameters for testing items to be analyzed using the reagents, and to readily verify that the analysis parameters have been correctly set, thereby improving the efficiency and reliability for the testing work conducted by the automatically analyzing apparatus. Also, when viewed from the reagent suppliers, it is expected to improve the efficiency in works related to the distribution of analysis parameters to testing facilities, and the like.

INDUSTRIAL AVAILABILITY

According to the present invention, analysis parameters can be readily set for testing items which are analyzed using reagents.

The invention claimed is:

1. An analysis information management method using a service center connected through communication lines to a plurality of automatic analyzing apparatuses used in a plurality of facilities, said service center having a database for storing analysis parameters related to a plurality of reagents for use in the plurality of automatic analyzing apparatuses used in the plurality of facilities, the method comprising the steps of:

creating, by said service center responsive to a request from one of said automatic analyzing apparatuses, a list of reagents available in said one automatic analyzing apparatus from information on reagents stored in said database, and supplying said one automatic analyzing apparatus with the list through a communication line;

transferring, by said service center responsive to a selection of an associated reagent from said list, made by a user of said one automatic analyzing apparatus, analysis parameters, according to which a test is to be carried out on a testing item to be analyzed using the selected reagent, to said one automatic analyzing apparatus through said communication line;

wherein said service center classifies and stores information, including results of calibrations measured by said automatic analyzing apparatuses, results of analyses on control samples, reagents used in analyses, and analysis parameters, for tests carried out in each facility or for each automatic analyzing apparatus, wherein the results of analyses on said control samples are derived from analyses of said control samples using the same reagents in all automatic analyzing apparatuses in all facilities administered by said service center;

calculating, by said service center based on the stored information on the results of analyses for each facility or for each automatic analyzing apparatus, a statistical standard value defined for said results of analyses on said control samples using the same reagents in all automatic analyzing apparatuses in all facilities administered by said service center;

adding said selected reagent to a control sample in said one automatic analyzing apparatus;

analyzing a control sample by said one automatic analyzing apparatus;

calculating, by said service center, a statistical deviation for the result of analysis from said standard value for evaluation; and determining, based on the calculated statistical deviation, whether the analysis parameters used in the analysis are correct.

2. An analysis information management method according to claim 1, wherein:
said automatic analyzing apparatus automatically sets the transferred analysis parameters.

3. An analysis information management method according to claim 1, wherein:
said database stores analysis parameters related to reagents from a plurality of reagent suppliers.

4. An analysis information management method according to claim 1, wherein:
when a reagent supplier supplies a novel reagent or a reagent in a new lot to a user of said one automatic analyzing apparatus, said reagent supplier registers said database with information related to said reagent, such as said reagent, automatic analyzing apparatuses capable of using said reagent, and analysis parameters for said reagent prior to supply.

5. An analysis information management method according to claim 1, wherein:
said service center, upon determination that the result of analysis on an accuracy management sample transferred thereto from said one automatic analyzing apparatus was derived using newly set analysis parameters, summarizes the result of determination in a report, and transmits the report to said one automatic analyzing apparatus through the communication line.

6. An analysis information management method according to claim 1, wherein:
each time said service center receives the result of analysis on a control sample from said one automatic analyzing apparatus, said service center calculates said statistical deviation from said standard value, and transmits the result of analysis to said one automatic analyzing apparatus through the communication line if any defect is recognized based on said determination.

7. An analysis information management method according to claim 6, wherein:
when no defect is recognized in the result of analysis, said service center stores the result of analysis, periodically creates a report, and transmits the report to the automatic analyzing apparatuses through the communication lines.

8. An analysis information management method according to claim 1, wherein:
said service center periodically calculates said standard value, and transmits said standard value to the automatic analyzing apparatuses through the communication lines as technical information.

9. An analysis information management method according to claim 1, wherein:
said service center stores and manages, by version, programs for controlling the automatic analyzing apparatuses administered thereby, and automatically installs a program of a requested version in response to a request from an automatic analyzing apparatus administered thereby.

* * * * *